(12) United States Patent
Seiki et al.

(10) Patent No.: US 7,470,348 B2
(45) Date of Patent: Dec. 30, 2008

(54) SEPARATOR FOR PRODUCING AROMATIC CARBOXYLIC ACIDS

(75) Inventors: Yoshio Seiki, Hiroshima (JP); Kazuto Kobayashi, Hiroshima (JP); Yoshiyuki Takeuchi, Hiroshima (JP); Hiroyuki Osora, Hiroshima (JP); Keiichi Akimoto, Tokyo (JP); Noritaka Matsumoto, Tokyo (JP); Motoki Numata, Kitakyusyu (JP); Hiroaki Shimazu, Matsuyama (JP)

(73) Assignees: Mitsubishi Heavy Industries, Ltd., Tokyo (JP); Mitsubishi Chemical Corporation, Tokyo (JP)

( * ) Notice: Subject to any disclaimer, the term of this patent is extended or adjusted under 35 U.S.C. 154(b) by 62 days.

(21) Appl. No.: 10/525,971

(22) PCT Filed: Aug. 29, 2003

(86) PCT No.: PCT/JP03/11122

§ 371 (c)(1),
(2), (4) Date: Sep. 27, 2005

(87) PCT Pub. No.: WO2004/020076

PCT Pub. Date: Mar. 11, 2004

(65) Prior Publication Data

US 2006/0135811 A1 Jun. 22, 2006

(30) Foreign Application Priority Data

Aug. 30, 2002 (JP) .............................. 2002-255663
Aug. 30, 2002 (JP) .............................. 2002-255664

(51) Int. Cl.
*B01D 3/32* (2006.01)
*B01D 71/02* (2006.01)

(52) U.S. Cl. .................. 202/182; 159/2.1; 159/DIG. 3; 159/DIG. 27; 159/DIG. 28; 202/197; 202/202; 210/151; 210/510.1

(58) Field of Classification Search ................. 159/2.1, 159/DIG. 3, DIG. 27, DIG. 28; 202/182, 202/185.1, 197, 202; 203/14–16, 98; 210/151, 210/510.1, 509

See application file for complete search history.

(56) References Cited

U.S. PATENT DOCUMENTS 4,562,285 A 12/1985 Hashizume et al.

(Continued)

FOREIGN PATENT DOCUMENTS

JP 53-84932 7/1978

(Continued)

*Primary Examiner*—Virginia Manoharan
(74) *Attorney, Agent, or Firm*—Wenderoth, Lind & Ponack, L.L.P.

(57) ABSTRACT

A separation system has a distillation column, an overhead vapor supply pipe connected to the top of the distillation column, first and second branch pipes branching from the overhead vapor supply pipe and a superheater connected to the first branch pipe. A separator downstream of the superheater has a separation membrane for separating overhead vapor from the top of the distillation column into permeable vapor and nonpermeable vapor by allowing only a selected portion of the overhead vapor to permeate the separation membrane. A reflux unit has a condenser connected to the second branch pipe for cooling a portion of the overhead vapor into a liquid and a gas-liquid separator for separating gas from the liquid produced by cooling and returning the separated liquid into the top of the distillation column.

5 Claims, 5 Drawing Sheets

U.S. PATENT DOCUMENTS

| | | | |
|---|---|---|---|
| 4,895,989 A * | 1/1990 | Sander et al. | 568/851 |
| 4,953,694 A * | 9/1990 | Hayashi et al. | 202/180 |
| 5,409,579 A | 4/1995 | Gualy et al. | |
| 5,427,687 A | 6/1995 | Blum et al. | |
| 5,492,625 A | 2/1996 | Wytcherley et al. | |
| 5,611,842 A * | 3/1997 | Friesen et al. | 95/50 |
| 7,048,833 B2 * | 5/2006 | Lumgair et al. | 203/1 |
| 2004/0191139 A1 | 9/2004 | Numata et al. | |
| 2004/0225148 A1 | 11/2004 | Isogai et al. | |
| 2006/0014979 A1 | 1/2006 | Numata et al. | |
| 2006/0151377 A1 | 7/2006 | Fujimoto et al. | |
| 2007/0131533 A1 * | 6/2007 | Blum et al. | 203/23 |

FOREIGN PATENT DOCUMENTS

| | | |
|---|---|---|
| JP | 60-202705 | 10/1985 |
| JP | 1-155928 | 6/1989 |
| JP | 2-253802 | 10/1990 |
| JP | 4-63119 | 2/1992 |
| JP | 7-53443 | 2/1995 |
| JP | 8-40972 | 2/1996 |
| JP | 2001-328957 | 11/2001 |
| WO | 96/06065 | 2/1996 |
| WO | 02/50012 | 6/2002 |

* cited by examiner

Fig.5 ized components in the nonpermeable vapor, too. Thus, it is possible to reduce the flow rate of the nonpermeable vapor returning to the distillation column, and thus the column size. In other words, it is possible to reduce the flow rate of the distillation column.

SEPARATOR FOR PRODUCING AROMATIC CARBOXYLIC ACIDS

TECHNICAL FIELD

The present invention relates to a method for producing an aromatic carboxylic acid by subjecting alkyl substituents or a partially oxidized aromatic alkyl compound to liquid-phase oxidation using an oxygen-containing gas, and a reactor used in this method.

BACKGROUND ART

Aromatic carboxylic acids are usually produced in an oxidation reactor by subjecting alkyl aromatic compounds as raw materials to liquid-phase oxidation in a solvent containing acetic acid in the presence of a catalyst containing a heavy metal compound and a bromine compound by use of a gas containing oxygen in the form of molecules. During this oxidizing reaction, water is produced. Reaction vapor discharged from the oxidation reactor and a mother liquid of aromatic carboxylic acid slurry contain reaction water. Such reaction vapor and mother liquid, the latter being obtained by separating aromatic carboxylic acids from the slurry produced, are typically dehydrated and distilled to recover acetic acid, which is recycled as a solvent for oxidation reaction.

Since water and acetic acid are difficult to separate from each other and because a dilute aqueous solution of acetic acid in particular has a specific volatility near 1, in order to separate acetic acid from water by dehydration and distillation so that the concentration of acetic acid in the distilled water will not exceed 1 weight percent, it is necessary to increase the number of stages of the distilling column and/or increase the reflux ratio. This increases the size of the dehydration/distillation column, which in turn pushes up its cost as well as the facility cost. Also, because the latent heat of vaporization of water is high, reboiler loads of distillation increases by increasing the reflux ratio. Various measures have been reported for avoiding this problem. For example, patent document 1 reports a method of reducing distillation loads by combining distillation with extraction. Patent document 2 reports that it is possible to reduce the reflux ratio and energy consumption by azeotropic distillation using an azeotropic agent in the dehydration/distillation column.

Also known are methods of dehydration in which a separation membrane such as a reverse osmosis membrane is used in distillation (patent documents 3 and 4). Patent document 3 proposes to remove water and alcohol by separation using a membrane in producing an aromatic carboxylic acid. With this arrangement, in which distillation is combined with separation using a membrane, it is possible to reduce loads on the dehydration/distillation column, so that an aliphatic carboxylic acid, a solvent, can be recovered with high efficiency.

The alcohol mentioned in patent document 5 is an unnecessary byproduct produced when recovering acetic acid by hydrolyzing an aliphatic carboxylic acid ester such as methyl acetate, which is a byproduct produced in the system. It is separated together with water by a membrane.

Patent document 1: JP patent publication 7-53443
Patent document 2: WO96-06065
Patent document 3: JP patent publication 2001-328957
Patent document 4: WO02-50012
Patent document 5: JP patent publication 2001-328957

DISCLOSURE OF THE INVENTION

As is apparent from patent documents 1 and 2, extraction agents and azeotropic agents are needed in the extraction and azeotropic methods, respectively. This complicates the dehydration/distillation steps. The methods disclosed in these references are therefore not sufficiently streamlined.

In an arrangement in which a separator membrane is used in distillation, such as disclosed in patent documents 3 and 4, it is an essential requirement to use a reverse osmosis membrane made of an organic material in the separation step. But organic high-molecular membranes, which are typically used as acid-resistant separator membranes that can selectively separate water from an aqueous solution containing organic acids, have a drawback in that their heat resistance is so poor that they can be used only at relatively low temperatures.

Further, because it is an effective means for minimizing the loss of an acetic acid solvent to reuse methyl acetate in the oxidation reaction step, the consumption of acetic acid will increase if alcohol is discharged out of the system by hydrolyzing an aliphatic carboxylic acid ester, as disclosed in patent document 5.

Still further, in this prior art, since any components that have not permeated the membrane is returned into the distillation column, components that have permeated the membrane are diluted at the top of the distillation column. This increases the amount of vapor and the amount of fluid flow in the distillation column, which in turn makes it necessary to increase the size of the distillation column and the area of the separator membrane. Also, it is necessary to re-heat the components that have not permeated the membrane and have been returned into the column. This requires additional energy consumption.

A general object of the invention is therefore to avoid all of the abovementioned problems, and its particular object is to provide a process for producing an aromatic carboxylic acid in which the step of removing water from a mixture of acetic acid and water that is produced during the process can be carried out using a facility of a reduced size with reduced energy consumption.

The present inventors sought ways to achieve this object and found out that by using a specific separator membrane, a mixture of acetic acid and water produced during a manufacturing process of an aromatic carboxylic acid can be efficiently separated into water and acetic acid, using a compact device with minimum energy consumption.

Specifically, the invention provides a separation system comprising: a distillation column into which a mixture of a first component mainly comprising water and a second component mainly comprising nonaqueous substances is adapted to be supplied; a separator including a separation membrane for separating overhead vapor discharged from a top of the distillation column into a permeable vapor which mainly comprises the first component and a nonpermeable vapor which mainly comprises the second component by allowing only a selected portion of the overhead vapor to permeate the separation membrane; and a reflux unit for cooling a portion of the overhead vapor into a liquid and returning the liquid thus obtained into an upper portion of the distillation column.

With this arrangement, by returning a portion of the overhead vapor into the distillation column through the reflux unit, it is possible to reduce the concentration of a high-boiling-point component in the overhead vapor (either the first or second component). Thus, the separation membrane has only to separate overhead vapor of which the concentration of a high-boiling-point component has decreased. This makes it possible to reduce the concentration of high-boilingpoint components in the vapor that has permeated the separation membrane to a required level.

In a second invention, the distillation column includes fluid beds.

In a third invention, there is provided a separation system comprising: a distillation column into which a mixture of a first component mainly comprising water and a second component mainly comprising nonaqueous substances is adapted to be supplied; a first separator including a first separation membrane for separating overhead vapor discharged from a top of the distillation column into a first permeable vapor which mainly comprises the first component and a first nonpermeable vapor which mainly comprises the second component by allowing only a selected portion of the overhead vapor to permeate the first separation membrane; and a second separator including a second separation membrane for separating the first permeable vapor into a second permeable vapor mainly comprising the first component and higher in the concentration of the first component than the first permeable vapor, and a second nonpermeable vapor which mainly comprises the second component by allowing only a selected portion of the first permeable vapor to permeate the second separation membrane.

After the overhead vapor has been separated into the first permeable vapor and the first nonpermeable vapor, the first permeable vapor is further separated into the second permeable vapor and the second nonpermeable vapor. Thus, most of the portion of the second component that may permeate the first separation membrane will be separated as the second nonpermeable vapor by the second separation membrane. Thus, it is possible to obtain a permeable condensed vapor high in the concentration of the first component as the second nonpermeable vapor.

According to a fourth invention, there is provided a reactor system comprising: a reactor for producing an aromatic carboxylic acid and water from an alkyl aromatic compound in a solvent containing acetic acid, and for generating a vapor mixture of a solvent and water; a first separation membrane for separating the vapor mixture, which is discharged from the reactor, into a first permeable vapor mainly comprising a first component and a first nonpermeable vapor mainly comprising a second component; a second separation membrane for separating the first permeable vapor, which is discharged from the first separation membrane, into a second permeable vapor mainly comprising the first component and a second nonpermeable vapor mainly comprising the second component; and a return passage for condensing and returning the first nonpermeable vapor and the second nonpermeable vapor into the reactor.

Any nonaqueous components that remain in the first permeable vapor without being separated by the first separation membrane are separated by the second separation membrane, recovered as the second nonpermeable vapor, and returned into the reactor. Thus, it is possible to reduce the water concentration in the reactor to less than a predetermined level, thereby accelerating reaction.

According to a fifth invention, the solvent containing acetic acid is acetic acid, the alkyl aromatic compound is paraxylene, and the aromatic carboxylic acid is terephthalic acid.

The reactor according to a sixth invention further comprises gas-liquid separators each provided between one of the first and second separation membranes and the return passage for separating terephthalic acid from the first and second nonpermeable vapors.

According to a seventh invention, the separation membrane or the first and second separation membranes comprise an inorganic porous member carrying in pores thereof a silica gel obtained by hydrolyzing an alkoxysilane containing ethoxy groups or methoxy groups.

According to an eighth invention, there is provided a method of producing an aromatic carboxylic acid comprising an oxidation reaction step in which an alkyl aromatic compound is reacted with a oxygen-containing gas in a solvent containing acetic acid in the presence of an oxidation catalyst to produce a slurry of the aromatic carboxylic acid; a solid-liquid separation step in which the slurry is separated into a reaction mother liquid and an aromatic carboxylic acid cake; and a step of separating at least a portion of a mixture of acetic acid and water produced during the steps into a permeable gas mainly comprising water and nonpermeable substances mainly comprising acetic acid, using a separation membrane capable of separating water.

In the step for producing an aromatic carboxylic acid using acetic acid as a solvent, water is produced as a byproduct during oxidation reaction. In distilling and separating acetic acid and water, since the evaporative latent heat of water is high, huge energy is needed. By separating the mixture into a permeable gas mainly comprising water and a nonpermeable substances mainly comprising acetic acid, using a membrane capable of separating water, i.e. a membrane that passes gaseous $H_2O$ molecules but is less likely to pass nonpermeable substances mainly comprising acetic acid, it is possible to reduce the energy needed to separate acetic acid from water.

According to a ninth invention, in the arrangement of the first invention, at least a portion of the mixture fed to the separation membrane is a gas. Since the substance that has permeated the separation membrane according to the invention is a gas, if the mixture is also a gas, it permeates the separation membrane more efficiently. By keeping the temperature of the mixture higher than the boiling point of acetic acid at the operation pressure when fed to the separation membrane, substantially the entire mixture can be supplied in the form of a gas. Thus, it is possible to separate a greater amount of mixture in a shorter period of time.

According to a tenth invention, the mixture of acetic acid and water contains methyl acetate, and at least a portion of the mixture is separated into a permeable gas mainly comprising water and nonpermeable substances mainly comprising acetic acid and methyl acetate. Since a separation membrane which can separate water is less likely to pass methyl acetate, it is present in the nonpermeable substances which mainly comprise acetic acid. Methyl acetate can thus be recovered together with acetic acid. This reduces the energy necessary to separate a mixture of acetic acid, methyl acetate and water into water and a mixture of acetic acid and methyl acetate.

According to an $11^{th}$ invention, in the third invention, the nonpermeable substances are at least partially returned to the oxidation reaction step. The nonpermeable substances, i.e. the substances that have not permeated the separation membrane, mainly comprise acetic acid and further contain methyl acetate. They scarcely contain water. On the other hand, oxidation reaction needs acetic acid as a solvent. Thus, by returning the nonpermeable substances as a solvent for oxidation reaction, acetic acid contained in the nonpermeable substances can be effectively used. Also, by recovering the methyl acetate contained in the nonpermeable substances, which is one of the byproducts of the oxidation reaction, in the oxidation step, it is possible to suppress the production of methyl acetate due to the equilibrium reaction of acetic acid, thereby reducing the loss of the solvent.

According to a $12^{th}$ invention, in the third invention, before membrane separation, the mixture is supplied into the distillation column, and at least part of acetic acid is recovered form the bottom of the column, and at least part of the mixture of acetic acid, methyl acetate and water which is discharged from the top of the column is supplied to the separation membrane, which is capable of separating water.

The larger the carboxylic acid production plant, the greater the amount of a mixture that has to be separated. In such a case, the mixture should be fed into a small distillation column beforehand to produce an overhead component having a reduced acetic acid content. By separating such an overhead component with a separation membrane, it is possible to reduce the energy required for separation.

According to a 13th invention, in the fifth invention, part of the mixture discharged from the top of the column is returned into the distillation column, and part of it is supplied to the separation membrane.

By returning part of the overhead component, its acetic acid content further decreases. Thus, by separating it through the separation membrane, it is possible to further reduce the energy for separation.

According to a 14th invention, in the fifth or sixth invention, the nonpermeable substances are returned to the oxidation reaction step. Thus, the methyl acetate contained in the nonpermeable substances can be recovered in the oxidation reaction step. This suppresses the production of methyl acetate during the equilibrium reaction of acetic acid, thereby reducing the loss of the solvent.

According to a 15th invention, the permeable gas mainly comprising water is further separated into a permeable gas mainly comprising water and nonpermeable substances mainly comprising acetic acid, using a separation membrane capable of separating water.

By providing the two separation membranes, the second separation membrane removes any organic components that have not been removed by the first separation membrane. High-purity water is thus obtained.

According to a 16th invention, in the eighth invention, one of the separation membranes that is provided upstream from the other is one that is higher in the permeating speed, and the other is one that is higher in the separation ability. With this arrangement, it is possible to separate the mixture of water and acetic acid in large amounts and with high purity.

According to a 17th invention, in the first invention, the separation membrane is made of an inorganic material. Since the membrane is formed of an inorganic material, it is durable and high in ability to separate water.

According to an 18th invention, in the ninth invention, the separation membrane or the separation membranes comprise an inorganic porous member carrying in pores thereof a silica gel obtained by hydrolyzing an alkoxysilane containing ethoxy groups or methoxy groups.

By using silica gel, it is possible to obtain water higher in purity.

According to a 19th invention, the alkyl aromatic compound is paraxylene, and the aromatic carboxylic acid is terephthalic acid. Today, among aromatic carboxylic acids, terephthalic acid is being produced in the greatest amount. Thus, plants for manufacturing terephthalic acid are increasing in size year after year. The present invention is most advantageously applicable to such plants.

According to the present invention, it is possible to reduce the size of systems for recovering solvents such as distillation columns and to reduce the energy consumed.

BEST MODE FOR EMBODYING THE INVENTION

The aromatic alkyl compound used in the invention is an alkyl benzene such as mono, di or trialkyl benzene, which is to be converted to an aromatic carboxylic acid such as aromatic monocarboxylic acid, aromatic dicarboxylic acid or aromatic tricarboxylic acid by liquid-phase oxidation, and include alkyl benzenes having their alkyl groups partially oxidized. The present invention is applicable especially to the production of a terephthalic acid. The aromatic alkyl compound used in the invention as the preferable raw material is a paraxylene.

Now description is made on how a terephthalic acid is produced by oxidizing a paraxylene.

Acetic acid as the solvent used in the invention is used in an amount 2 to 6 times in weight of the paraxylene, the raw material. This acetic acid solvent may contain a small amount, i.e. not more than 15 percent by weight, of water.

In order to oxidize the paraxylene in a liquid phase, a gas containing molecular oxygen is used, which is typically air because air can be used at a low cost with a simple facility. Air may be diluted or enriched with oxygen.

In oxidizing the paraxylene, a catalyst containing cobalt (Co), manganese (Mn) and bromine (Br) as its constituent elements is usually used.

The paraxylene is oxidized in a liquid phase by continuously supplying a gas containing molecular oxygen at 140-230 degrees Celsius, preferably 150-210 degrees Celsius in the presence of a catalyst in the acetic acid solvent. The pressure during the oxidation step has to be at least high enough for the mixture to be capable of maintaining a liquid phase at the reaction temperature, and is typically in the range of 0.2 to 5 MPa, preferably 1 to 2 MPa.

The reactor is typically a tank having an agitator. But an agitator is not an essential element. For example, it may be a bubble tower. It has a port for a molecular oxygen-containing gas at its lower portion.

A molecular oxygen-containing gas that has been supplied into the reactor through its port is used for oxidation, and leaves the reactor as an exhaust gas carrying a large amount of solvent vapor.

The reaction product obtained in the reaction step is formed into a reaction slurry, of which the temperature and the pressure is reduced to suitable levels in a crystallization step to obtain a terephthalic acid slurry. The crystallization is carried out in 1 to 6 steps, preferably in 2 to 4 steps. In the crystallization step, flush cooling is employed. The final step is preferably carried out in a reduced-pressure, boiled state.

Typically, the slurry that has been subjected to crystallization is subjected to a solid-liquid separation step and a drying step to recover a terephthalic acid. The terephthalic acid thus recovered may consist of a low-purity terephthalic acid and a medium-purity terephthalic acid. But the low-purity terephthalic acid may be further refined to a high-purity terephthalic acid. In this case, after replacing the acetic acid solvent with an aqueous solvent in a solvent replacement step, the low-purity terephthalic acid may be directly sent to the refining step, while bypassing the drying step.

In the solvent recovering step, the mother liquid that has been aliquoted in the solid-liquid separation step, and oxidized exhaust gas or its condensate are refined, typically distilled, to obtain acetic acid.

Using a separation membrane having preference for water, at least part of a mixture of acetic acid, methyl acetate byproducts and reaction water produced in the oxidation step, solid-liquid separation step and solvent recovering step is separated into a permeable gas of which the major component is water and a nonpermeable substances of which acetic acid and methyl acetate are main components to recover methyl acetate and acetic acid.

Separation membranes 8, 46, 84 and 86 (FIGS. 1-3) according to the present invention, which have preference for water, are membranes that preferentially pass water ($H_2O$) molecules. That is, when a mixture of water and organic compounds is fed through such membranes, water can more easily permeate them than the organic compound molecules. More specifically, these separation membranes have a vapor-acetic acid separation coefficient $\alpha$ in the range of about 200 to 500 if the vapor concentration is 20 to 40 weight percent. (The separation coefficient $\alpha$ is expressed by $\alpha=\{(1-Y)/Y\}/\{(1-X)/X\}$, where X is the molar fraction of the nonpermeative components before permeating the membrane, and Y is the molar fraction of the nonpermeative components after permeating the membrane.)

Such separation membranes can separate e.g. a mixture of acetic acid and water into a permeable gas consisting essentially of aqueous substances of which the major component is water and nonpermeable substances mainly comprising nonaqueous substances such as acetic acid as a main component.

In the preferred embodiment, mixtures fed through separation membranes are gases. Such gases include gases discharged from the oxidation reactor and gases obtained during dehydration/distillation treatment in the solvent recovering step. Such gases further include gases obtained by directly supplying exhaust gases from the oxidation reactor directly into a distillation column and dehydrating them, and gases obtained by cooling, while releasing pressure, a condensate obtained by condensing at least part of the abovementioned gases.

By feeding such a gas mixture of acetic acid and water through one of the separation membranes of the invention, the gas mixture can be separated into a permeable gas consisting essentially of aqueous substances and a nonpermeable gas consisting essentially of nonaqueous substances.

If such a gas mixture contains an organic compound or an inert gas in addition to acetic acid and water, when it permeates one of the separation membranes of the invention, such an organic compound or inert gas will preferentially remain in the nonpermeable substances, which consist essentially of nonaqueous substances, because such an organic compound or inert gas is less permeable through the membrane.

Figure 5:
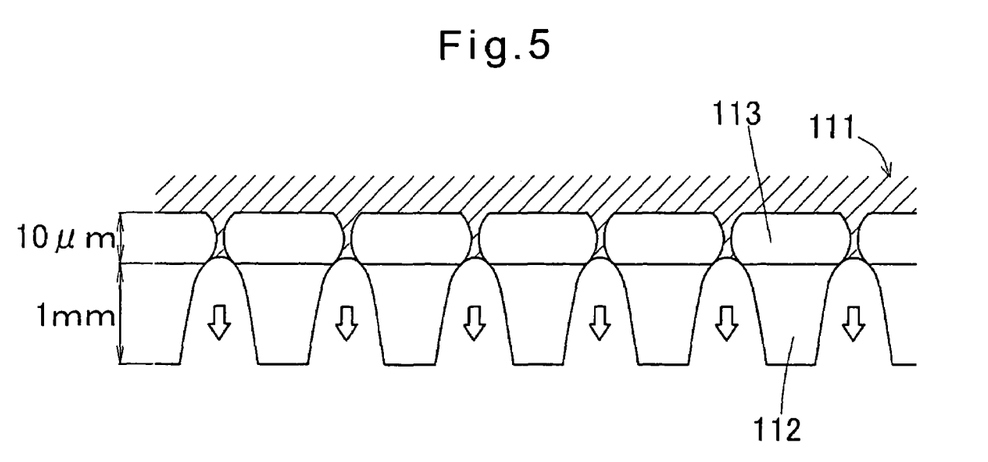

Any of the separation membranes according to the present invention, designated by 111 in FIG. 5, is made of an inorganic material. Specifically, it comprises an inorganic porous member 112 such as a porous ceramic substrate, about 1 mm thick, and a silica gel carrying layer 113 comprising a silica gel membrane about 10 micrometers thick. The separation membrane may be a flat, tubular or otherwise shaped member. The silica gel is not limited but is preferably one obtained by hydrolyzing an alkoxysilane containing ethoxy groups or methoxy groups because it improves preference for water.

To such a separation membrane, water ($H_2O$) is preferentially adsorbed by —OH groups in the silica gel carrying layer 113, thereby inhibiting other components from finding their way into the pores of the silica gel carrying layer 113. The water adsorbed by the —OH groups moves in the pores and permeates the silica gel carrying layer 113. Thus, the —OH groups in the silica gel carrying layer 113 serve to selectively separate and remove water in vapor. As a result, the separation membrane reveals preference for water.

Now embodiments of the invention are described. Throughout the specification, the aqueous component mainly comprising water is referred to as the "first component", and the nonaqueous component mainly comprising acetic acid, methyl acetate and the like is referred to as the "second component".

EMBODIMENT 1

Figure 1:
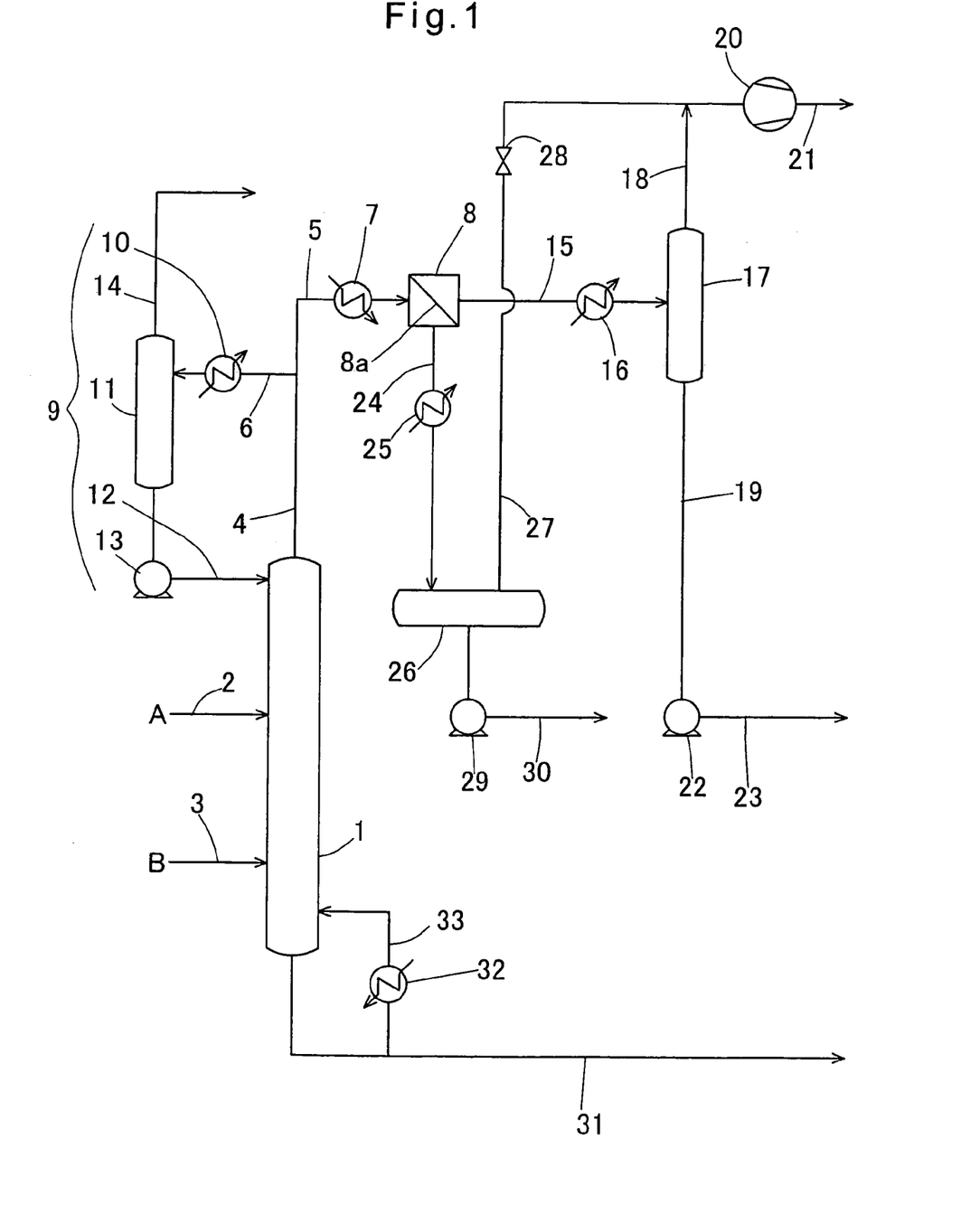
FIG. 1 is a diagrammatic view of a separation system of a first embodiment according to the present invention for separating a solution mixture.

FIG. 1 shows Embodiment 1 of the present invention, which is a separation system for separating a solution of a mixture of water and acetic acid.

Typically, the separation system of Embodiment 1 is used to remove water produced by oxidation reaction when producing a terephthalic acid by oxidizing, in a liquid phase, a paraxylene as the raw material using air in a reaction solvent containing acetic acid in the presence of an oxidation catalyst.

The separation system of Embodiment 1 includes a distillation column 1 having a plurality of fluidized beds such as shelves in the interior thereof. To an upper portion of the column, 78 weight percent of a liquid-phase aqueous solution of acetic acid (liquid-phase feed) is supplied through an upper supply pipe 2, and to a lower portion of the column, 87 weight percent of an aqueous solution of acetic acid and a small amount of nitrogen are supplied as a vapor-phase feed through a lower supply pipe 3. Thus, a mixture of the first and second components is supplied into the distillation column 1.

An overhead vapor supply pipe 4 is connected to the top of the distillation column 1 such that overhead vapor from the column 1 is introduced into the supply pipe 4. The pipe 4 branches to a first branch pipe 5 and a second branch pipe 6. In Embodiment 1, overhead vapor is distributed to the first branch pipe 5 and the second branch pipe 6 in the ratio of e.g. 9 to 1. A superheater 7 for superheating the overhead vapor is mounted to the downstream end of the first branch pipe 5. Provided further downstream from the superheater 7 is a separator 8 including a separation membrane 8a for separating the overhead vapor into a permeable vapor mainly comprising steam (first component) and nonpermeable substances mainly comprising acetic acid vapor (second component).

In this embodiment, the separation membrane 8a is made of an inorganic material. It passes water or water vapor relatively freely but scarcely passes acetic acid or acetic acid vapor.

The second branch pipe 6 includes a reflux unit 9 comprising a condenser 10 for cooling and liquefying the overhead vapor flowing into the pipe 6, a gas-liquid separator 11 for separating the thus cooled overhead vapor into gas and liquid, and a liquid-phase pump 13 for returning the separated liquid into the distillation column 1 through a return pipe 12. Gas separated in the gas-liquid separator 11 is discharged through a discharge pipe 14.

The vapor that has permeated the separation membrane 8a of the separator 8 flows into a vapor introducing pipe 15 connected to the separator 8, and is cooled and liquefied in a condenser 16 provided in the pipe 16. The thus cooled vapor is separated into gas and liquid in a gas-liquid separator 17 connected to the pipe 15. The gas separated in the separator 17 is discharged through a discharge pipe 18 and a vacuum pump 20 into a gas discharge pipe 21. The liquid separated in the separator 17 is discharged through a discharge pipe 19 and a liquid-phase pump 22 into a liquid discharge pipe 23.

Nonpermeable vapor that has not permeated the separation membrane 8a of the separator 8 flows into a nonpermeable vapor introducing pipe 24 connected to the separator 8, and is cooled and liquefied in a condenser 25 provided in the pipe 24. The thus cooled vapor is separated into gas and liquid in a gas-liquid separator 26 connected to the pipe 24. Gas separated in the separator 26 is discharged through a discharge pipe 27 and a pressure valve 28 into the vacuum pump 20 and the gas discharge pipe 21. Liquid separated in the separator 26 is discharged through a liquid-phase pump 29 and a first acetic acid discharge pipe 30.

To the bottom of the distillation column 1, a second acetic acid discharge pipe 31 is connected through which the bottom layer of the liquid in the distillation column 1, which is high in acetic acid concentration, is discharged. Part of the liquid flowing into the pipe 31 flows into a circulating pipe 33 extending from an intermediate portion of the pipe 31 to the distillation column 1, is reheated in a reboiler 32 provided in the pipe 33, and is returned into the distillation column 1.

Separation steps performed by the separating system of Embodiment 1 are now described.

First, the liquid-phase feed A and the vapor-phase feed B are fed through the upper supply pipe 2 and lower supply pipe 3, respectively, into the distillation column 1. Since the liquid-phase feed A falls in the distillation column 1 and the vapor-phase feed B rises in the column 1, they will contact each other in the column 1. Part of the liquid discharged through the second acetic acid discharge pipe 31 is heated by the reboiler 32 and returned into the distillation column 1 near its bottom through the circulating pipe 33.

The liquid-phase feed A is a liquid substance of which primary components are water and acetic acid. The vapor-phase feed B is a gaseous substance or a liquid substance that is gasified in the column 1 and primarily comprises water and acetic acid. The vapor-phase feed B also includes a substance that remains liquid in the column but is gasified when heated by the reboiler 32 or the reboiler 74 in Embodiment 2.

When the feeds A and B are fed into the column, they will be mixed together such that water concentration is higher near the top of the distillation column 1 and the acetic acid concentration is higher near the bottom of the column 1.

Overhead vapor (of which the water concentration is relatively high) flows into the overhead vapor introducing pipe 4, and is then distributed into the first branch pipe 5 and the second branch pipe 6 in the proportion of 9 to 1.

Overhead vapor that has been introduced into the second branch pipe 6 is returned into the distillation column 1 by the reflux unit 9. The vapor thus returned into the column 1 further increases the water concentration and thus reduces the acetic acid concentration near the top of the column 1.

Overhead vapor introduced into the first branch pipe 5 is superheated in the superheater 7 (to prevent the overhead vapor from being liquefied before reaching the separation membrane 8a), and introduced into the separator 8.

The thus superheated overhead vapor is separated into a permeable vapor mainly comprising water and a nonpermeable vapor mainly comprising acetic acid.

The reflux unit 9 serves to reduce the acetic acid concentration of the overhead vapor introduced into the first branch pipe 5 to a substantially constant value (about 62 weight percent). The acetic acid concentration of the permeable vapor that has permeated the separation membrane 8a thus decreases to less than 1 weight percent.

The permeable vapor is cooled in the condenser 16 and mostly liquefied. After removing nitrogen gas and other gases mixed in the liquid in the gas-liquid separator 17, the liquid is fed by the liquid-phase pump 22 and recovered.

The nonpermeable vapor is cooled in the condenser 25 and mostly liquefied. After removing nitrogen gas and other gases mixed in the liquid in the gas-liquid separator 26, the liquid is fed by the liquid-phase pump 29 and recovered.

Gaseous components removed from the vapor in the gas-liquid separators 17 and 26 are sucked by the vacuum pump 20 and discharged from the system. The pressure valve 28 prevents the nonpermeable vapor from flowing toward the gas-liquid separator 17 even if the nonpermeable vapor pressure is higher than the permeable vapor pressure.

The permeable vapor thus produces water containing not more than 1 weight percent of acetic acid, while the nonpermeable vapor produces a liquid comprising not less than 93 weight percent of acetic acid. The liquid produced from the permeable vapor is useful in the plant. Or even if it is discarded, it will not contaminate the environment because it is practically pure water. The nonpermeable vapor and the liquid discharged from the lower portion of the distillation column 1 have enough purity as solvents to be used in the process. When discharged from the top of the distillation column 1, the overhead vapor contains methyl acetate, which is a byproduct produced during oxidation reaction. It is separated as the nonpermeable vapor together with acetic acid in the separator 8. The nonpermeable gas, which contains acetic acid and methyl acetate, is recovered and reused in the oxidation step. This reduces the consumption of acetic acid.

In Embodiment 1, the reflux unit 9 is provided to reduce the acetic acid concentration of the overhead vapor. Thus, separation of the overhead vapor can be carried out so as to meet the requirements of the user according to the separation capability of the separation membrane 8a. The separated liquid need not be returned into the distillation column 1. This makes it possible to use a smaller distillation column 1 and save energy.

In Embodiment 1, both the liquid-phase feed and the vapor-phase feed are supplied into the distillation column 1. But only one of them may be supplied.

In Embodiment 1, a mixed solution is distilled in the distillation column 1. But if it is desired to reduce the size of the entire separation system, the distillation column 1 may be replaced with an evaporating can.

EMBODIMENT 2

Figure 2:
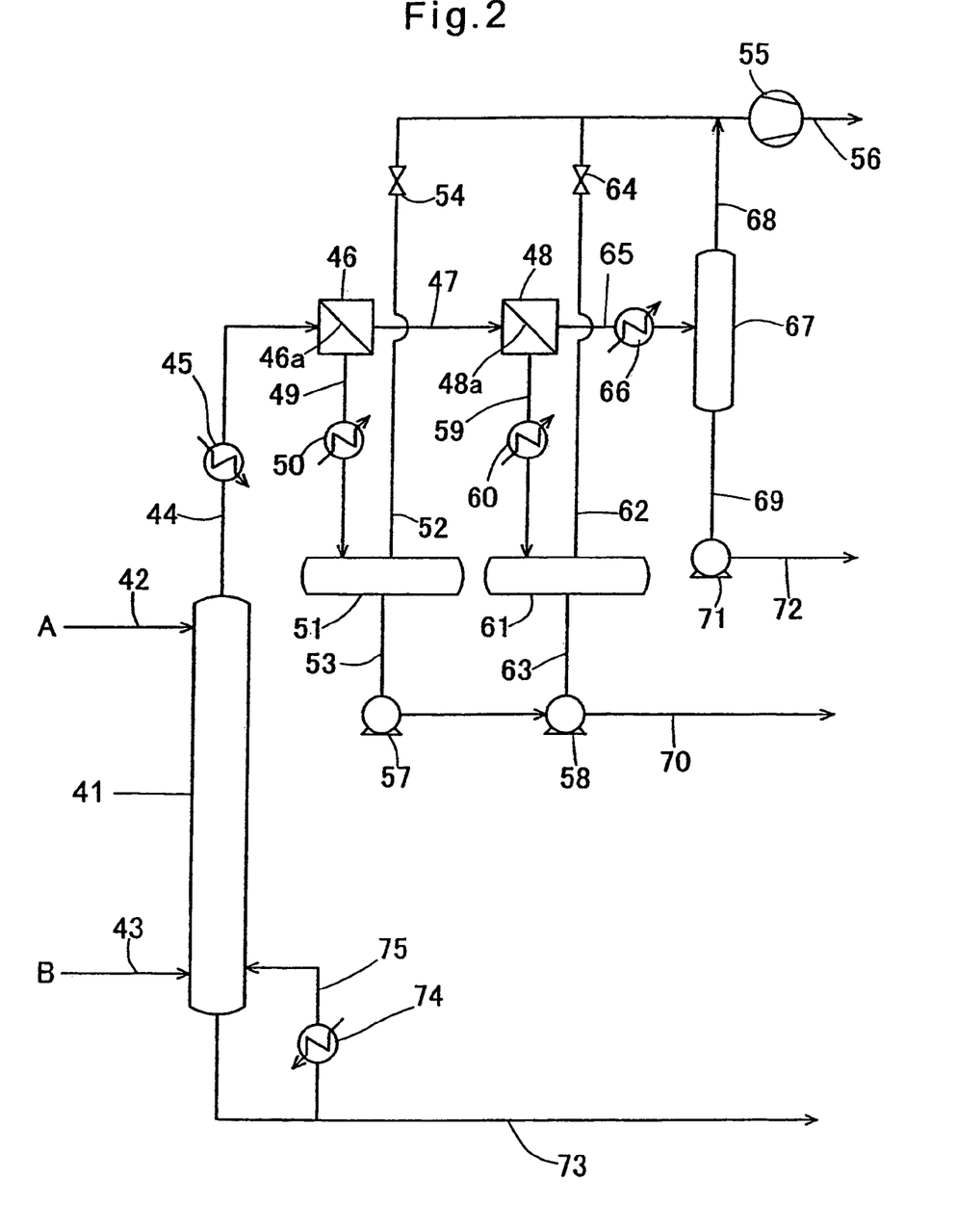
FIG. 2 is a diagrammatic view of similar separation system of a second embodiment of the present invention.

FIG. 2 shows Embodiment 2 of the present invention, which is a separation system for separating a solution of a mixture of water and acetic acid.

Like the system of Embodiment 1, the system of Embodiment 2 is typically used to remove water produced by oxidation reaction when producing a terephthalic acid by oxidizing, in a liquid phase, a paraxylene as the raw material using air in a reaction solvent containing acetic acid in the presence of an oxidation catalyst.

Like the system of Embodiment 1, the system of Embodiment 2 includes a distillation column 41 having a plurality of fluid beds such as shelves in the interior thereof. To an upper portion of the column, 78 weight percent of a liquid-phase aqueous solution of acetic acid (liquid-phase feed A) is supplied through an upper supply pipe 42, and to a lower portion of the column, 87 weight percent of an aqueous solution of acetic acid and a small amount of nitrogen are supplied as a vapor-phase feed B through a lower supply pipe 43.

To the top of the distillation column 41, an overhead vapor introducing pipe 44 is connected into which overhead vapor spontaneously flows from the top of the distillation column

41. To the downstream end of the pipe 44, a superheater 45 for superheating the overhead vapor is connected. Downstream from the superheater 45, a first separator 46 is provided which includes a first separation membrane 46a for separating the overhead vapor into a first permeable vapor mainly comprising steam and a first nonpermeable vapor mainly comprising acetic acid vapor.

The first separation membrane 46a is identical to the separation membrane 8a of Embodiment 1.

The first permeable vapor, which has permeated the first separation membrane 46a, is introduced into a first permeable gas introducing pipe 47 connected to the first separator 46. The first permeable gas introducing pipe 47 is provided with a second separator 48 including a second separation membrane 48a for separating the first permeable vapor into a second permeable vapor containing, as its major component, a first component of the first permeable vapor in a higher concentration than the first permeable vapor, and into a second nonpermeable vapor containing, as its major component, a second component of the first permeable vapor. The second separation membrane 48a is identical to the first separation membrane 46a. A superheater (not shown) may be provided between the first separator 46 and the second separator 48 to superheat the first permeable vapor.

The first nonpermeable vapor, i.e. the vapor that has not permeated the first separation membrane 46a of the first separator 46, is introduced into a first nonpermeable vapor introducing pipe 49 connected to the first separator 46. The pipe 49 is provided with a condenser 50 for cooling and liquefying the first nonpermeable vapor. The thus liquefied first nonpermeable gas is then separated into gas and liquid in a gas-liquid separator 51 connected to the pipe 49. The gas separated in the separator 51 is introduced into a discharge pipe 52 connected to the separator 51, while the liquid separated in the separator 51 is introduced into a discharge pipe 53 connected to the separator 51. The discharge pipe 52 is connected through a pressure valve 54 to a vacuum pump 55 and a gas discharge pipe 56. The discharge pipe 53 is connected through a first liquid-phase pump 57 and a second liquid-phase pump 58 to a first acetic acid discharge pipe 70.

The second nonpermeable vapor, i.e. the vapor that has not permeated the second separation membrane 48a of the second separator 48, is introduced into a second nonpermeable vapor introducing pipe 59 connected to the second separator 48. The pipe 59 is provided with a condenser 60 for cooling and liquefying the second nonpermeable vapor. The thus cooled and liquefied vapor is separated into gas and liquid in a gas-liquid separator 61 connected to the pipe 59. Gas separated in the separator 61 flows into a discharge pipe 62 connected to the separator 61, while liquid separated in the separator 61 flows into a discharge pipe 63 connected to the separator 61. The discharge pipe 62 is connected through a pressure valve 64 to the vacuum pump 55. The discharge pipe 63 is connected to the second liquid-phase pump 58.

The second permeable vapor, i.e. the vapor that has permeated the second separation membrane 48a of the second separator 48, is introduced into a second permeable vapor introducing pipe 65 connected to the separator 48, and is cooled and liquefied in a condenser 66 provided in the pipe 65. The thus cooled and liquefied second permeable vapor is separated into gas and liquid in a gas-liquid separator 67 connected to the pipe 65. Gas separated in the separator 67 is introduced into the discharge pipe 68 connected to the separator 67, while liquid separated in the separator 67 flows into a discharge pipe 69 connected to the separator 67. The discharge pipe 68 connects to the vacuum pump 55. The discharge pipe 69 connects to a water discharge pipe 72 through a third liquid-phase pump 71.

To the bottom of the distillation column 41, a second acetic acid discharge pipe 73 is connected through which the lowermost layer of the liquid in the distillation column 41, which is high in acetic acid concentration, is discharged. Part of the liquid flowing into the pipe 73 flows into a circulating pipe 75 extending from an intermediate portion of the pipe 73 to the distillation column 1, is reheated in a reboiler 74 provided in the pipe 75, and returned into the distillation column 41.

Now the operation of the system of Embodiment 2 is described.

First, the liquid-phase feed and the vapor-phase feed are fed through the upper supply pipe 42 and lower supply pipe 43, respectively, into the distillation column 41. Since the liquid-phase feed falls in the distillation column 41, and the vapor-phase feed rises in the column 41, they contact each other in the column 41. Part of the liquid discharged through the second acetic acid discharge pipe 73 is heated by the reboiler 74 and returned into the distillation column 41 near its bottom through the circulating pipe 75.

When the feeds are fed into the column, they are distributed in the column such that the water concentration is higher near the top of the distillation column 41 and the acetic acid concentration is higher near its bottom.

Overhead vapor (of which the water concentration is relatively high) flows into the overhead vapor introducing pipe 44, is superheated in the superheater 45 (to prevent the overhead vapor from being liquefied before reaching the separation membrane 46a), and is introduced into the first separator 46.

The thus superheated overhead vapor is separated into a first permeable vapor mainly comprising water and a first nonpermeable vapor mainly comprising acetic acid.

In Embodiment 2, in order to increase the water concentration of the overhead vapor to a certain extent, the liquid-phase feed is introduced into the upper portion of the distillation column 41. Still, the acetic acid concentration of the first permeable vapor is sufficiently high (about 68 percent by weight).

The first permeable vapor is introduced into the second separator 48, and separated into a second permeable vapor mainly comprising water, and a second nonpermeable vapor mainly comprising acetic acid.

Since the acetic acid concentration of the first permeable vapor is about 5 percent by weight as described above, the acetic acid content of the vapor that has permeated the second separation membrane 48a decreases to less than 1 percent by weight.

The second permeable vapor is cooled in the condenser 66 and mostly liquefied. After removing nitrogen gas and other gases mixed in the liquid in the gas-liquid separator 67, the liquid is fed by the third liquid-phase pump 71 and recovered.

The first separation membrane 46a of the first separator 46 and the second separation membrane 48a of the second separator 48 are both capable of separating water. In order to ensure both high separation speed and high separation ability, the first separation membrane 46a is preferably one which is high in permeating speed, while the second separation membrane 48a is preferably one high in separation ability.

The second nonpermeable vapor is cooled in the condenser 60 and mostly liquefied. After removing nitrogen gas and other gases mixed in the liquid in the gas-liquid separator 61, the liquid is fed by the second liquid-phase pump 58 and recovered.

The first nonpermeable vapor, which has not permeated the first separator 46, is cooled in the condenser 50 and mostly liquefied. After removing nitrogen gas and other gases mixed in the liquid in the gas-liquid separator 51, the liquid is fed by the first and second liquid-phase pumps 57 and 58 and recovered.

The second permeable vapor thus produces water containing not more than 1 percent by weight of acetic acid, while the first nonpermeable vapor and the second nonpermeable vapor produce a liquid containing 95 percent by weight of acetic acid. A liquid discharged from the bottom of the distillation column 41 contains 98 percent by weight of acetic acid. The liquid produced from the second permeable vapor is useful in the plant. Or even if it is discarded, it will not contaminate the environment because it is practically pure water. The first and second nonpermeable vapor and the liquid discharged from the bottom of the distillation column 41 have enough purity as solvents to be used in the process. The overhead vapor discharged from the top of the distillation column 41 contains methyl acetate, which is produced during oxidation reaction. It is separated as the nonpermeable vapor together with acetic acid in the first and second separators 46 and 48. The nonpermeable vapors, which contain acetic acid and methyl acetate, are recovered and reused in the oxidation step. This reduces the consumption of acetic acid.

In Embodiment 2, the first and second separators 46 and 48 are provided to separate the overhead vapor in the first separator 46, and then re-separate the first permeable gas, i.e. vapor that has permeated the first separation membrane 46a with the second separation membrane 48a to obtain the second permeable vapor. Thus, the liquid obtained from the second permeable vapor has improved purity. The liquids obtained from the first nonpermeable vapor, i.e. vapor that has not permeated the first separation membrane 46a, and the second nonpermeable vapor, i.e. vapor that has not permeated the second separation membrane 48a, also have enough purity. Since the liquids produced from these separated vapors are all high in purity, they do not have to be returned into the distillation column 41. This makes it possible to use a smaller distillation column 41 and save energy.

In Embodiment 2, both the liquid-phase feed and the vapor-phase feed are supplied into the distillation column 41. But only the liquid-phase feed may be supplied.

In Embodiment 2, a mixed solution is distilled in the distillation column 41. But if it is desired to reduce the size of the entire separation system, the distillation column 41 may be replaced with an evaporating can.

In Embodiment 2, the first permeable vapor, i.e. the vapor that has permeated the first separation membrane 46a, is re-separated with the second separation membrane 48a. But according to the capacity of the separation membranes, the concentration of the mixed solution and other conditions, a different arrangement may be employed. For example, the first nonpermeable vapor, i.e. the vapor that has not permeated the first separation membrane 46a, may be re-separated with the second separation membrane 48a.

In Embodiment 2, too, the reflux unit 9 of Embodiment 1 may be used.

EMBODIMENT 3

Figure 3:
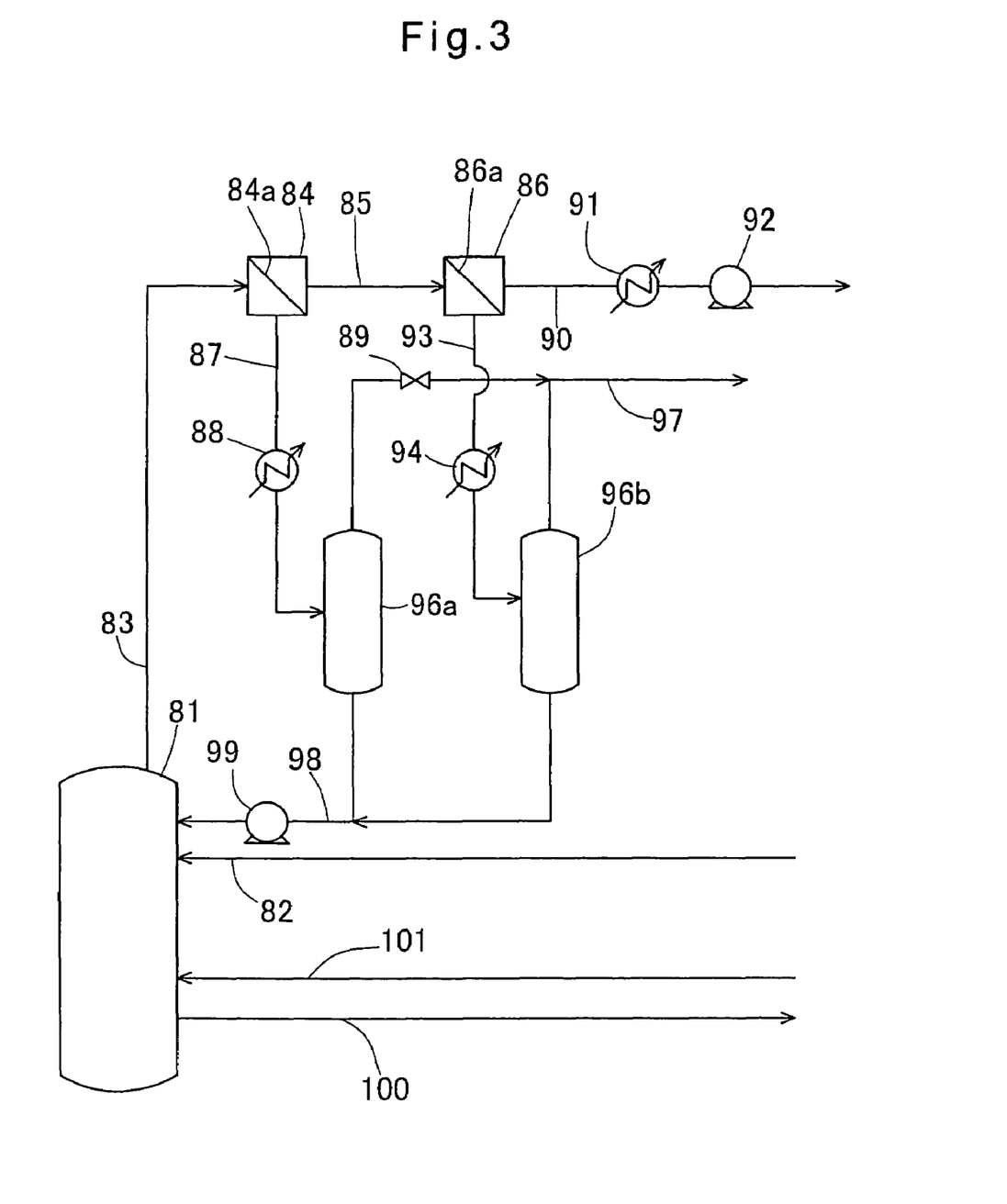
FIG. 3 is a diagrammatic view of a third embodiment of the present invention, which is a reactor system.

FIG. 3 shows Embodiment 3, which is a reactor system for synthesizing terephthalic acid according to the present invention.

This reactor system includes a reactor 81 filled with an oxidation catalyst for paraxylene (such as a cobalt compound). To the reactor 81, a raw material supply pipe 82 is connected through which paraxylene as the raw material, an acetic acid solvent, and an oxidation catalyst are supplied into the reactor. To the top of the reactor 81, a reaction vapor discharge pipe 83 is connected through which reaction vapor produced in the reactor is discharged. Air as an oxidant is supplied into the reactor 81 through an oxidant supply pipe 101.

To the reaction vapor discharge pipe 83, a first separator 84 including a first separation membrane 84a is connected. The first separation membrane 84a is identical to the separation membrane 8a of Embodiment 1. Thus, it passes a first component which mainly comprises steam, but does not pass a second component containing acetic acid vapor and other organic components.

The interior of the reactor 81 is kept at 1-2 MPa and at a temperature of 100 to 200 degrees Celsius. The vapor supplied through the reaction vapor discharge pipe 83 to the first separation membrane 84a contains steam, acetic acid vapor and vapor of other organic components, besides gaseous components derived from the air supplied and gaseous components produced during the reaction.

First permeable vapor, i.e. the vapor that has permeated the first separation membrane 84a of the first separator 84 (of which the major component is water), is introduced into a first permeable vapor introducing pipe 85 connected to the separator 84. To the first permeable vapor introducing pipe 85, a second separator 86 including a second separator membrane 86a is connected. The second separation membrane 86a is identical to the first separation membrane 84a. A superheater (not shown) may be provided between the first and second separators 84 and 86 to superheat the first permeable vapor. The second separator 86 separates the first permeable vapor into a second nonpermeable vapor comprising a nonaqueous substance of which the major component is the solvent in the first permeable vapor and a second permeable vapor mainly comprising water.

First nonpermeable vapor, i.e. the vapor that has not permeated the first separation membrane 84a of the first separator 84 (of which main components are acetic acid solvent, other organic components and gas components derived from the air supplied and reaction gas components) is introduced into a first nonpermeable vapor introducing pipe 87 connected to the separator 84. The pipe 87 is provided with a condenser 88 and a pressure regulating valve 89.

Second permeable vapor, i.e. the vapor that has permeated the second separation membrane 86a of the second separator 86 (of which the major component is water) is introduced into a second permeable vapor introducing pipe 90 connected to the separator 86. The pipe 90 is provided with a condenser 91 and a liquid-phase pump 92.

Second nonpermeable vapor, i.e. the vapor that has not permeated the second separation membrane 86a of the second separator 86 (of which main components are acetic acid solvent, other organic components and gas components derived from the air supplied and reaction gas components) is introduced into a second nonpermeable vapor introducing pipe 93 connected to the separator 86. The pipe 93 is provided with a condenser 94 and a pressure regulating valve.

The first and second nonpermeable vapor introducing pipes 87 and 93 are connected to gas-liquid separators 96a and 96b, respectively. Gas components (such as oxygen, nitrogen, carbon dioxide and carbon monoxide in Embodiment 3) separated in the separators 96a and 96b are discharged through a gas discharge pipe 97 connected to the separators 96a and 96b, while liquid components (acetic acid solvent and other organic components) separated in the separators 96a and 96b are returned into the reactor 81 through a liquid discharge pipe 98 connected to the separators 96a and 96b. The first and second nonpermeable vapor introducing pipes 87 and 93, condensers 88 and 94, gas-liquid separators 96a and 96b and liquid discharge pipe 98 form a return passage. A liquid-phase pump 99 may be provided in the return passage as shown.

To a lower portion of the reactor 81, a product discharge pipe 100 is connected through which an acetic acid slurry of terephthalic acid present in the form of a liquid in the reactor 81 is discharged.

Figure 4:
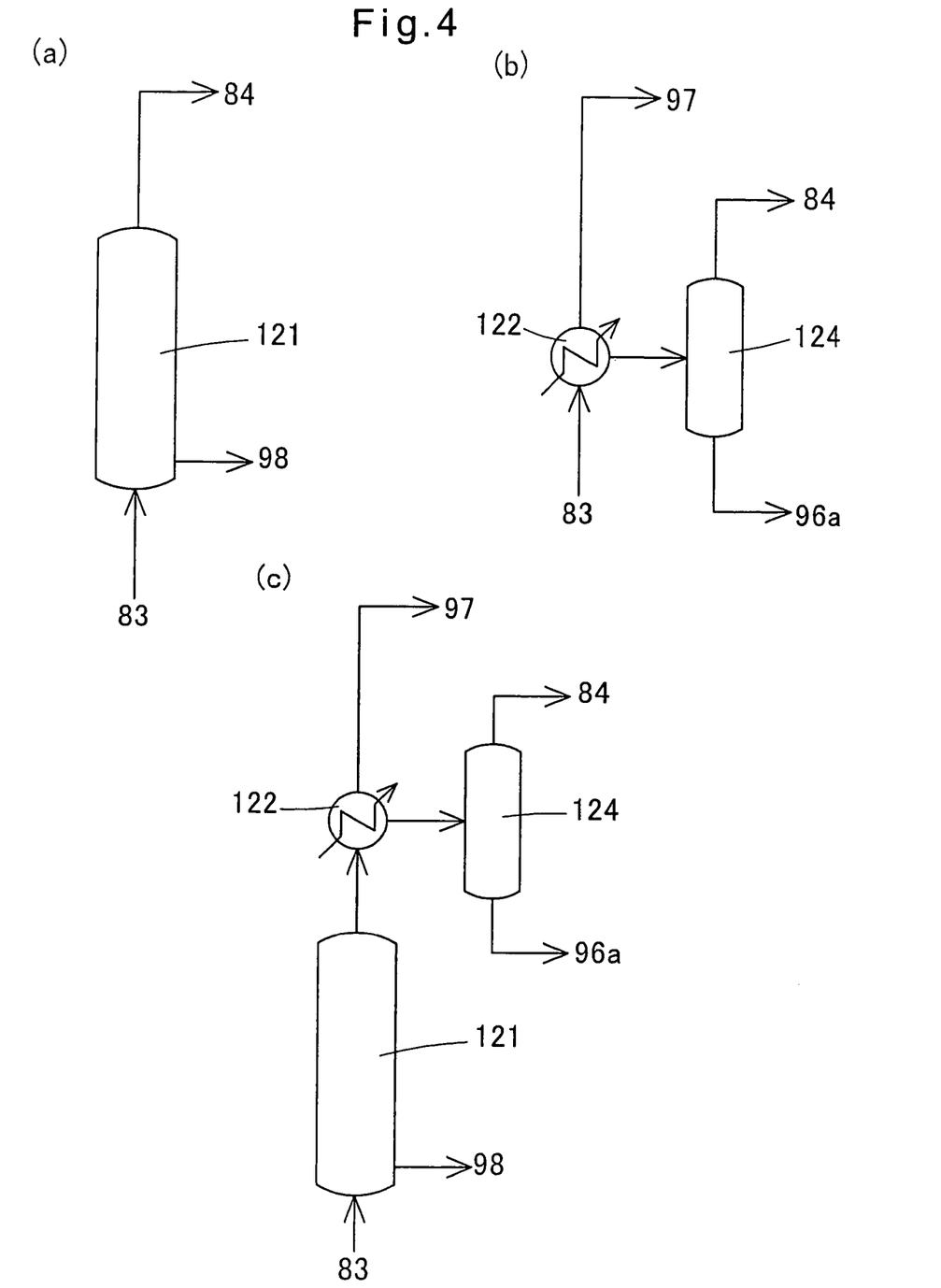
FIGS. 4A-4C are diagrammatic views of modified examples of the third embodiment, and FIG. 5 schematically shows a separation membrane.

In Embodiment 3, to the reaction vapor discharge pipe 83, through which vapor produced in the reactor 81 flows, a distillation unit 121 may be connected as shown in FIG. 4A. In this arrangement, vapor discharged from the reactor 81 is supplied into the distillation unit 121 and distilled therein to recover an acetic acid component. Also, gas containing a smaller amount of acetic acid is discharged from the top of the distillation unit 121. The gas thus produced is supplied to the first separator 84. The acetic acid component recovered from the distillation unit 121 is fed into the liquid discharge pipe 98 and thus returned into the reactor 81. Thus, the distillation unit 121 serves to reduce the acetic acid component in the vapor to be supplied to the first separator 84.

In Embodiment 3, to the reaction vapor discharge pipe 83, through which the vapor produced in the reactor 81 flows, a condenser 122 may be connected as shown in FIG. 4B. The condenser 122 serves to condense any condensable components contained in the vapor discharged from the reactor 81. Any components that are not condensed by the condenser 122 are fed into the gas discharge pipe 97.

Any components condensed in the condenser 122 are at least partially evaporated in an evaporator 124, and the evaporated components are fed optionally to the first separator 84 through a heater. Any components that are not evaporated in the evaporator 124 are fed to the gas-liquid separator 96a. The condenser 122 and the evaporator 124 make it possible to treat any noncondensable components contained in the vapor discharged from the reactor 81 while bypassing the first separator 84.

The evaporator 124 is not limited provided it can at least partially evaporate the liquid condensed in the condenser 122. For example, if the liquid condensed in the condenser 122 is under pressure, the evaporator 124 is preferably a flush tank, a tank which is kept at a lower pressure than in the condenser 122.

In Embodiment 3, as shown in FIG. 4C, the distillation unit 121 shown in FIG. 4A may be connected to the reaction vapor discharge pipe 83, through which the vapor discharged from the reactor 81 flows, and further the condenser 122 shown in FIG. 4B may be connected to a discharge pipe extending from the distillation unit 121. This arrangement has both of the functions of the arrangements of FIGS. 4A and 4B.

Now the operation of Embodiment 3 or the reactor system according to the present invention is described.

A paraxylene solution is supplied into the reactor 81 through the raw material supply pipe 82 together with an acetic acid solvent. Air as an oxidant is supplied through the oxidant supply pipe 101. In the reactor 81, paraxylene is oxidized by the action of a catalyst, producing terephthalic acid and water. Through the reaction vapor discharge pipe 83, a vapor mixture (about 150-200 degrees Celsius) of water, acetic acid solvent, other organic components, gas components derived from the supplied air, and reaction gas components is discharged.

The vapor mixture discharged from the reactor 81 is introduced into the first separator 84 through the reaction vapor discharge pipe 83, and is separated by the first separation membrane 84a into the first permeable vapor, of which the major component is water, and the first nonpermeable vapor, of which main components are acetic acid solvent, other organic components, gaseous components derived from the supplied air, and reaction gas components.

In Embodiment 3, as in Embodiment 1, the separation ability of the first separation membrane 84a is such that the first permeable vapor inevitably contains certain amounts of acetic acid solvent, other organic compounds, gaseous components derived from the supplied air, and reaction gas components.

However, the first permeable vapor is fed to the second separator 86 through the first permeable vapor introducing pipe 85, and separated again by the second separation membrane 86a into the second permeable vapor, of which the major component is water and the second nonpermeable vapor, of which main components are acetic acid solvent, other organic components, gaseous components derived from the supplied air, and reaction gas components. Thus, the second permeable vapor is practically pure water. The second permeable vapor is introduced into the second permeable vapor introducing pipe 90, liquified in the condenser 91, fed under pressure by the liquid-phase pump 92 and recovered in the form of water.

The first and second nonpermeable vapors, of which main components are acetic acid solvent, other organic components, gaseous components derived from the supplied air, and reaction gas components, are introduced into the first and second nonpermeable vapor introducing pipes 87 and 93, condensed in the condensers 88 and 94, and fed into the gas-liquid separators 96a and 96b, respectively.

The first separation membrane 84a of the first separator 84 and the second separation membrane 86a of the second separator 86 are both capable of separating water. In order to ensure both high separation speed and separation ability, the first separation membrane 84a is preferably one which is high in permeating speed, while the second separation membrane 86a is preferably one which is high in separation ability.

In the gas-liquid separators 96a and 96b, gas components mixed in the first nonpermeable vapor and the second nonpermeable vapor (which mainly comprise gaseous components derived from the supplied air and reaction gas components) are separated and discharged through the gas discharge pipe 97. Liquid components (which mainly comprise acetic acid solvent and other organic components) are discharged through the liquid discharge pipe 98, optionally pressurized in the liquid-phase pump 99, and returned into the reactor 81 (i.e. to the oxidation step) through the raw material supply pipe 82.

Terephthalic acid produced in the reaction during the oxidation step is discharged through the product discharge pipe in the form of an acetic acid slurry and recovered. It may be refined to obtain high-purity terephthalic acid.

What is claimed is:

1. A separation system comprising:
 a distillation column into which a mixture of a first component mainly comprising water and a second component mainly comprising nonaqueous substances is supplied;
 an overhead vapor supply pipe connected to a top of said distillation column;
 first and second branch pipes branched from said overhead vapor supply pipe;
 a superheater connected to said first branch pipe;
 a separator provided downstream of said superheater and including a separation membrane for separating overhead vapor discharged from the top of said distillation column into a permeable vapor which mainly comprises said first component and a nonpermeable vapor which mainly comprises said second component by allowing only a selected portion of said overhead vapor to permeate said separation membrane; and a reflux unit comprising a condenser connected to said second branch pipe for cooling a portion of said overhead vapor into a liquid and a gas-liquid separator for separating gas from the liquid produced by cooling in said condenser and returning the thus separated liquid into the top of said distillation column.

2. The separation system of claim 1 wherein said distillation column includes fluidized beds.

3. The separation system of claim 1 wherein said separation membrane comprises an inorganic porous member comprising a porous ceramic substrate, and a silica gel layer comprising a silica gel membrane carried on the surface of the porous ceramic substrate or in the pores of the porous ceramic substrate.

4. A separation system comprising:

a distillation column into which a mixture of a first component mainly comprising water and a second component mainly comprising nonaqueous substances is supplied;

an overhead vapor supply pipe connected to a top of said distillation column;

first and second branch pipes branched from said overhead vapor supply pipe;

a superheater connected to said first branch pipe;

a first separator provided downstream of said superheater and including a first separation membrane for separating overhead vapor discharged from the top of said distillation column into a permeable vapor which mainly comprises said first component and a nonpermeable vapor which mainly comprises said second component by allowing only a selected portion of said overhead vapor to permeate said separation membrane;

a second separator including a second separation membrane for separating said first permeable vapor into a second permeable vapor which mainly comprises said first component and is higher in the concentration of said first component than said first permeable vapor, and a second nonpermeable vapor which mainly comprises said second component, by allowing only a selected portion of said first permeable vapor to permeate said second separation membrane; and a reflux unit comprising a condenser connected to said second branch pipe for cooling a portion of said overhead vapor into a liquid, and a gas-liquid separator for separating gas from the liquid produced by cooling in said condenser, and returning the thus separated liquid into the top of said distillation column.

5. The separation system of claim 4 wherein said first and second separation membranes each comprise an inorganic porous member comprising a porous ceramic substrate, and a silica gel layer comprising a silica gel membrane carried on the surface of the porous ceramic substrate or in the pores of the porous ceramic substrate.

* * * * *